(12) United States Patent
Marasco

(10) Patent No.: US 8,418,696 B2
(45) Date of Patent: Apr. 16, 2013

(54) ARM BOARD PATIENT SECUREMENT ARRANGEMENT

(76) Inventor: Patrick V. Marasco, Boxford, MA (US)

( * ) Notice: Subject to any disclaimer, the term of this patent is extended or adjusted under 35 U.S.C. 154(b) by 21 days.

(21) Appl. No.: 13/136,960

(22) Filed: Aug. 16, 2011

(65) Prior Publication Data

US 2013/0046155 A1   Feb. 21, 2013

(51) Int. Cl.
A61F 5/37 (2006.01)
A61F 5/00 (2006.01)
A61B 19/00 (2006.01)

(52) U.S. Cl.
USPC .............. 128/877; 128/878; 128/869; 602/20

(58) Field of Classification Search .................. 128/877, 128/869, 846, 878, 845, 879, 112.1, 882, 128/880; 602/12, 20, 21; 604/393, 391; 2/910, 24, 20

See application file for complete search history.

Primary Examiner — Patricia Bianco
Assistant Examiner — Victoria J Hicks
(74) Attorney, Agent, or Firm — Don Halgren

(57) ABSTRACT

An arm board securement arrangement for comfortably and safely securing a patient's arm to an arm board during an operative procedure, comprising a flexible sheet of conformable material having a first end and a second end, and a first side and a second side with a central portion therebetween. A plurality of spaced apart wrap members extend from the central portion on the first side thereof. A plurality of spaced apart wrap members extending on the second side from the central portion. A gripping or securement member is arranged on each of the wrap members to permit the wrap members to correspondingly engage one another about an arm of a patient.

13 Claims, 3 Drawing Sheets

ARM BOARD PATIENT SECUREMENT ARRANGEMENT

BACKGROUND OF THE INVENTION

1. Field of the Invention

The present invention relates to securement arrangements for patients undergoing a surgical procedure on an operating table having armboards and more particularly to comfortable devices for holding a patient in a proper safe orientation in a surgical operating field.

2. Discussion of Prior Art

Arm boards are articulated platforms arranged on the sides of surgical tables utilized in operating rooms. These boards may swing or articulate from the sides of the operating table to permit a patient's arms to be rested thereon. The patient's arms are typically secured to the table by a narrow strap of Velcro™ risk nerve injury. These straps commonly utilized in the prior art will often crimp the patient's arm and/or shut off the patient's circulation in that arm being restrained. These straps however are necessary to keep the position of the patient's arms and body secure and keep the patient from moving around during a surgical procedure. These straps also to keep the patient from falling off of the side of the operating table.

Further however, these straps must permit access to the patient's arms to provide anesthesia lines and or patient monitoring lines to be maintained in place.

It is an object of the present invention to overcome the disadvantages of the prior art.

It is a further object of the present invention to provide a secure and arrangement for arm boards which will be comfortable and safe for the patient, provide proper securement to maintain the patient in proper position on the operating table and provide access to the patient's arms for treatment lines fed thereto.

It is yet a still further object of the present invention to provide an arm board strap arrangement which provides warmth and comfort to the patient while the patient is on the operating table.

BRIEF SUMMARY OF THE INVENTION

The present invention comprises an arm board arm securement arrangement for use in surgical settings such as operating rooms in hospitals. The arm board securement arrangement comprises an elongated flexible strap member having a first or distalmost end and a second or proximalmost end with a longitudinally directed axis extending down its middle. The flexible strap member has a first or top wrap member side and a second or lower wrap member side edge portion thereon. The flexible strap member has a longitudinal length of about the length of an armed board utilized in a surgical setting. That length is about 1½ feet. The side to side width of the flexible strap member is preferably about 2½ feet.

The first side of the flexible strap member has a plurality of spaced apart dedicated-shape wrap members. Each wrap member on the first side of the securement flexible strap member has a width of about 3 inches, and a length of about 9 inches. The space between adjacent wrap members is about 2 inches.

The second side of the flexible strap member has a first and a second spaced apart dedicated shape wrap member and a third or elongated dedicated shape wrap member spaced apart from the second wrap member, as well. The first, second and third wrap members (a wrist/hand member, a forearm member and an upper arm member, respectively) on the second side of the flexible strap member are shorter than the spaced apart wrap members on the first side of the flexible strap arrangement. Those first second and third wrap members on the second side of the strap arrangement are for example, about 8 inches long.

The arm board securement arrangement has a central portion which is about 15 inches wide. A plurality of openings are spaced along the longitudinal axis of the central portion of the securement arrangement so as to expose portions of the arm board beneath the arm board securement arrangement through the securement arrangement. An articulated arm board extending from the surgical table has an upper surface which is covered with an attachment layer means, such as for example, of Velcro™ loops (or hooks).

The spaced apart wrap members on the first side of the arm board securement arrangement each have a patch of Velcro™ hooks (or loops) on an upper side thereof adjacent their distal edge. The spaced apart wrap members on the second side of the arm board securement arrangement each preferably have a patch of Velcro™ loops on a lower side thereof adjacent to their distal edge.

When a patient may be undergoing a surgical procedure on an operating table, that patient's arm(s) would be held out to the side of that table and held supported by those articulable arm boards extending therefrom. The arm board securement arrangement would it be placed on the arm board for both or either of the patient's left arm and right arm as necessary. Each left arm and right arm securement arrangement are mirror images of one another.

The arm board securement arrangement is laid upon the arm board so as to expose the Velcro™ loops of the arm board through the elongated array of openings extending longitudinally down the central portion of the arm board securement arrangement. An elongated armboard pillow is placed over the central portion of the arm board securement arrangement. The elongated pillow has a lower surface thereon covered with an array of attachment means thereon, such as for example, Velcro™ hooks. The Velcro™ hooks attached themselves to the Velcro™ loops which are exposed through the central openings of the arm board securement arrangement. The patient's arm is thus comfortably adjusted so as to rest upon the articulated arm board and the pillow resting upon the arm board securement arrangement. The elongated first, second and third wrap members from the second side of the arm aboard securement arrangement are brought over the each respective portion of the patient's arm, with the Velcro™ loops on the distal portions thereof now facing upwardly. The elongated first, second, third and fourth wrap members from the first side of the arm board securement arrangement are drawn over the first, second and third wrap members from the second side of the arm board securement arrangement. The Velcro™ now-downwardly facing hook "patches" on the first, second, third and fourth wrap members from the first side of the arm board securement arrangement are secured to the now-upwardly facing loops "patches" from the first, second and third wrap members from the second side of the arm board securement arrangement, to also permit a universally and an ongoingly adjustment capability to comfortable and safely secure each of the patient's limbs on an arm board. The longitudinal spacing between the spaced apart wrap members also permits access to the exposed skin of the patient's arm secured therewithin. Thus medicaments and surgical monitoring arrangements may be utilized in conjunction with a comfortable securement arrangement for a patient's arm for a patient undergoing a surgical procedure.

In a further embodiment of the present invention, the arm board securement arrangement may include a built-in blood pressure monitor, a pulse oximeter, a thermometer apparatus or the like, and/or a properly supplied heating circuit or cooling circuit, to conveniently support, monitor and maintain comfort and provide needed treatment needs of a patient undergoing a procedure on a surgical operating table utilizing the armed board securement arrangement of the present invention.

The invention thus comprises an arm board securement arrangement for comfortably and safely securing a patient's arm to an arm board during an operative procedure, comprising: a flexible sheet of conformable material having a first end and a second end, and a first side and a second side with a central portion therebetween; a plurality of spaced apart wrap members extending on the first side from the central portion; a plurality of spaced apart wrap members extending on the second side from the central portion; and a gripping patch arranged on each of the members to permit the members to correspondingly engage one another about an arm of a patient. wherein the central portion has a plurality of spaced apart openings therethrough. The arm board securement preferably includes an elongated pillow for disposition upon an upper surface of the central portion for the resting of a patient's arm thereon. The elongated pillow has a lower central portion engaging surface with gripping means thereon, to engage a gripping means arranged upon an upper surface of an arm board on which the securement arrangement is placed. The spaced apart wrap members on the first side are longer than the wrap members arranged on the second side of the central portion. The central portion has a longitudinal axis, and is preferably about one and one-half feet long, about the length of an arm board. In one aspect of the present invention, a blood pressure monitor may be arranged across the central portion to permit a patient's blood pressure to be monitored while the patient's arm is safely and comfortably secured to an arm board. Further, an oximeter may also be arranged across the central portion to permit a patient's blood to be monitored while the patient's arm is safely and comfortably secured to an arm board. The wrap members are spaced apart about 2 inches to permit access to the patient's skin while the patient's arm is comfortably and safely secured to an arm board. The wrap members of the first side of the central portion are for example, about 3 inches wide to permit safe wrapping of a patient's arm and prevent digging in of a strap and hurt the patient's circulation.

The invention also may comprise a method of securing a patient's arm to an operating table's armboard extending therefrom, comprising: placing a flexible sheet of conformable material having a first end and a second end, and a first side and a second side with a central portion there-between and a longitudinal axis extending therealong onto an armboard of an operating table, the conformable material having a plurality of spaced apart wrap members extending on the first side from the central portion, with a plurality of spaced apart wrap members extending on the second side from the central portion; and a gripping patch arranged on each of the members to permit the members to correspondingly engage one another about an arm of a patient; wrapping the wrap members from the first side of the conformable material over on top of the patient's arm on the arm board; wrapping the wrap members from the second side of the conformable material on top of the wrap members from the first side of the conformable material; and securing the wrap members from the first side onto the wrap members from the second side by interengagement with their respective gripping patches so as to hold the patient's arm to the arm board in a comfortable and secure manner. The invention may include installing a patient sensor onto the upper side of the conformable material to permit the patient's medical tests to be safely and easily run on the patient, and inserting a pillow between the patient's arm and the conformable material, and attaching gripping securment means on the upper surface of the arm board, and running a medical test on a patient secured to the arm board through the sensor incorporated onto the conformable material.

The invention may also comprise an arm board securement arrangement for comfortably and safely securing a patient's arm to an arm board during an operative procedure, comprising: a flexible sheet of conformable material having a first end and a second end, and a first side and a second side with a central portion therebetween and a longitudinal axis extending therealong; a plurality of spaced apart wrap members extending on the first side from the central portion of the conformable material; a plurality of spaced apart wrap members extending on the second side from the central portion of the conformable material; a gripping patch arranged on each of the wrap members to permit the members to universally adjustably and correspondingly engage one another upon the wrap members being wrapped about an arm of a patient; and a patient treatment member arranged within the securement arrangement to provide patient's treatment needs. The treatment member may comprise a patient temperature adjustment circuit. The treatment member may comprise a patient monitoring system. The treatment member may also comprise a patient medicament supply circuit therein.

BRIEF DESCRIPTION OF THE DRAWINGS

The objects and advantages of the present invention will become more apparent, when viewed in conjunction with the following drawings in which.

DETAILED DESCRIPTION OF THE PRESENT INVENTION

Figure 1:
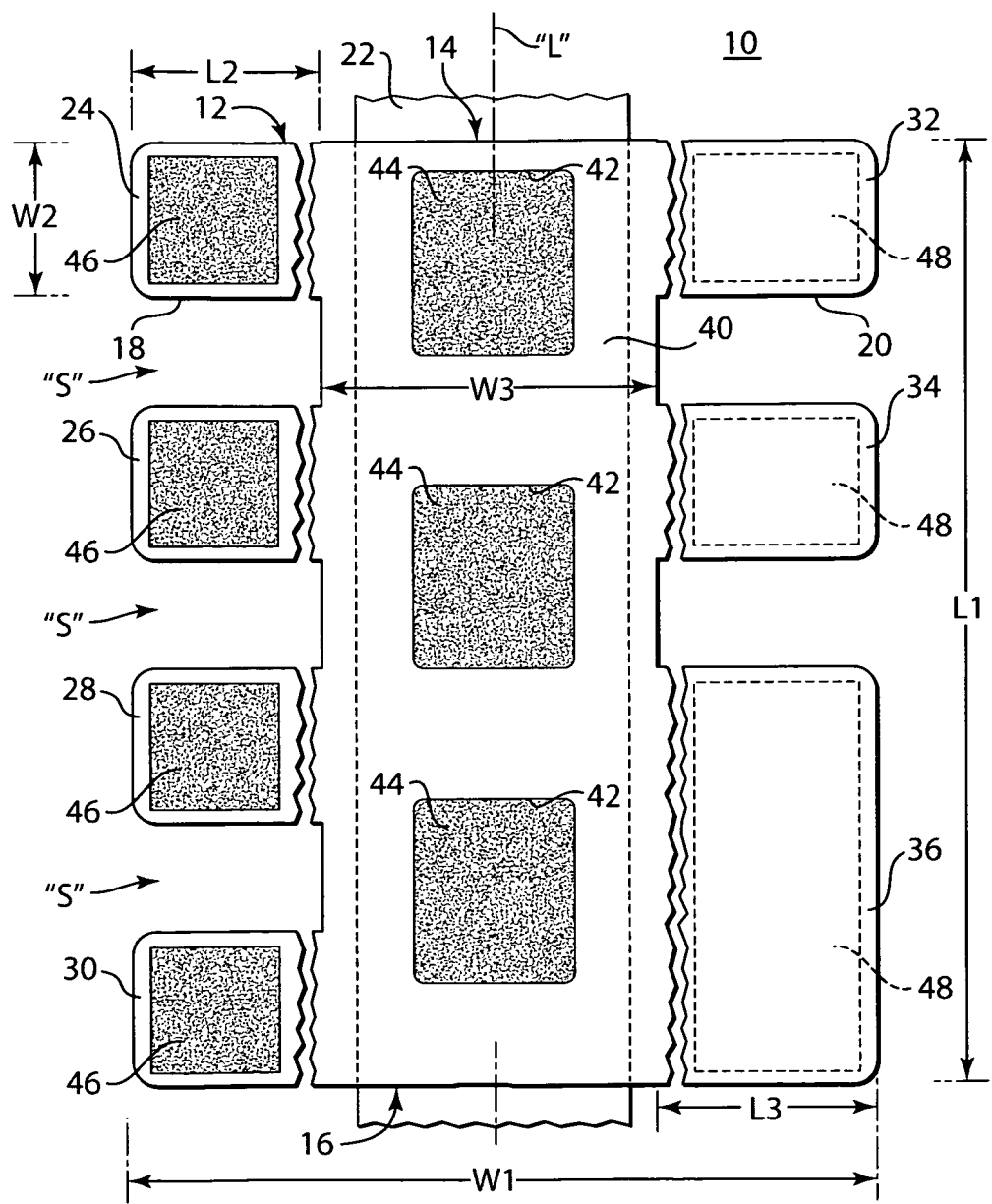
FIG. 1 is a plan view of an arm board securement arrangement lain out in planar fashion on an extended arm board of a surgical table.
Figure 2:
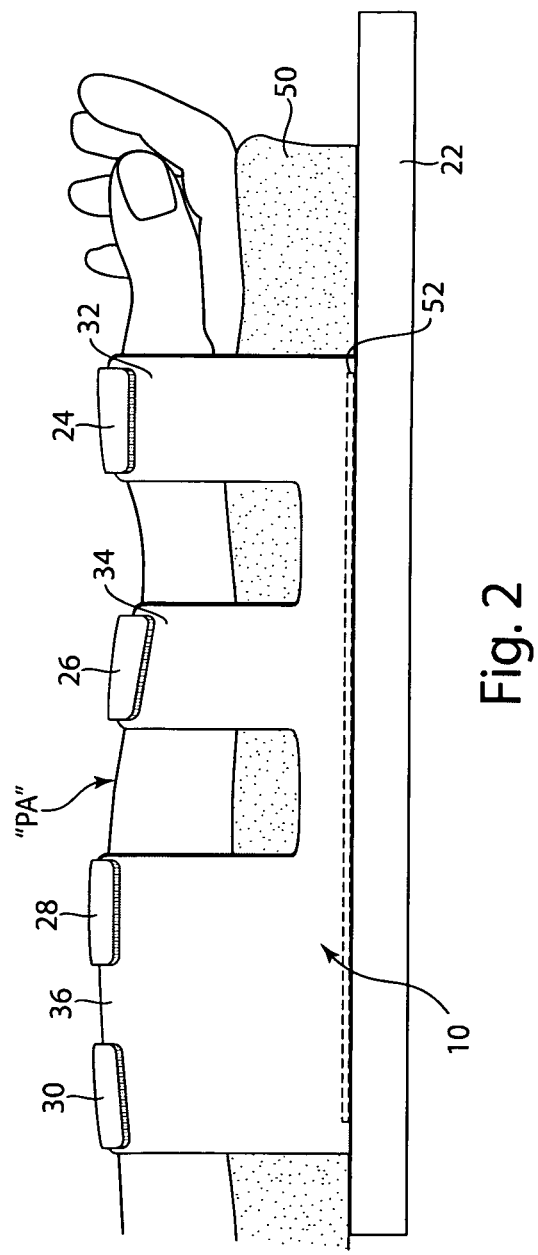
FIG. 2 is a side elevation of view of a patient's arm resting on a pillow and supported on an extended arm board and secured thereto by the arm board securement arrangement of the present invention.

The present invention comprises an arm board arm securement arrangement 10, as represented in FIGS. 1 and 2, for use in surgical settings such as operating rooms in hospitals. The arm board securement arrangement 10 comprises an elongated flexible strap member having a first or distalmost end 14 and a second or proximalmost end 16 with a longitudinally directed axis "L" extending down its middle, as represented in FIG. 1. The flexible strap member 12 has a first or top wrap member side 18 and a second or lower wrap member side edge portion 20 thereon. The flexible strap member 12 has a longitudinal length "L1" of about the length of an armed board 22 utilized in a surgical setting. That length is about 1½ feet. The side to side width "W1" of the flexible strap member (securement arrangement) is preferably about 2½ feet.

The first side 18 of the securement arrangement 10 has a plurality of spaced apart wrap members 24, 26, 28 and 30, as shown in FIG. 1. Each wrap member 24, 26, 28 and 30 on the first side 18 of the securement arrangement 10 has a width "W2" of about 3 inches, and a length "L2" of about 9 inches.

The rectilinear space "S" between adjacent wrap members 24, 26, 28 and 30 is about 2 inches wide.

The second side 20 of the securement arrangement 10 has a first and a second spaced-apart wrap member 32 and 34, and a third or elongated wrap member 36, spaced apart from the second wrap member 34, as well, as may be seen in FIGS. 1 and 2. The first, second and third wrap members 32, 34 and 36 on the second side 20 of the securement arrangement 10 are shorter than the spaced-apart wrap members 24, 26, 28 and 30 on the first side 18 of the securement arrangement 10. Those first, second and third wrap members 32, 34 and 36 on the second side 20 of the securement arrangement 10 have a length "L3" of preferably about 8 inches.

The arm board securement arrangement 10 has a rectilinear central portion 40 having a width "W3" of about 15 inches, as shown in FIG. 1. A plurality of openings 42 are spaced along the longitudinal axis of the central portion 40 so as to expose portions of the arm board 22 beneath the arm board securement arrangement 10. An articulated arm board 22 extending from the surgical table has an upper surface with at least a portion of which is covered with a layer of universally adjustable attachment members, for example, Velcro™ loops 44, as represented in FIG. 1.

The spaced apart wrap members 24, 26, 28 and 39 on the first side 18 of the arm board securement arrangement 10 each preferably have for example, a "patch" of Velcro™ hooks 46 on an upper facing side thereof adjacent their distal edge, as represented in FIG. 1. The spaced apart wrap members 32 on the second side 20 of the arm board securement arrangement 10 each have a patch of Velcro™ loops 48 on a lower side thereof adjacent to their distal edge, as are represented in phantom lines in FIG. 1.

When a patient may be undergoing a surgical procedure on an operating table, that patient's arm(s) would be held out to the side of that table and held supported by those articulable arm boards 10 (only one being shown for clarity of figures) extending therefrom. The arm board securement arrangement 10 would it be placed on the arm board 22 for both or either of the patient's left arm and right arm as necessary. Each left arm and right arm securement arrangement are mirror images of one another.

The arm board securement arrangement 10 is laid upon the arm board 22, as represented in FIG. 1 so as to expose the Velcro™ loops 44 of the arm board 22 through the elongated array of openings 42 extending longitudinally down the central portion 40 of the arm board securement arrangement 10. An elongated arm board pillow 50, as represented in FIG. 2 is placed over the central portion 40 of the arm board securement arrangement 10. The elongated pillow 50 has a lower surface 52 thereon covered with an array of Velcro™ hooks, not shown for clarity of figures. The Velcro™ hooks attached themselves to the Velcro™ loops 44 (or reversed) which are exposed through the central openings 42 of the arm board securement arrangement 10. The patient's arm "PA" is thus comfortably adjusted so as to rest upon the articulated arm board 22 and the pillow 50 resting upon the arm board securement arrangement 10, as shown in FIG. 2. The elongated first, second and third wrap members 32, 34 and 36 from the second side 20 of the arm aboard securement arrangement 10 are brought over the upper portion of the patient's arm PA, with the Velcro™ loops 48 on the distal portions thereof now facing upwardly. The elongated first, second, third and fourth wrap members 24, 26, 28 and 30, from the first side 18 of the arm board securement arrangement 10 are drawn snugly and adjustably over the first, second and third wrap members 32, 34 and 36 from the second side 20 of the arm board securement arrangement 10, as represented in FIG. 2. The Velcro™ now-downwardly facing hook patches 46 on the first, second, third and fourth wrap members 24, 26, 28 and 30 from the first side 18 of the arm board securement arrangement 10 are secured to the now-upwardly facing loop patches 48 from the first, second and third wrap members 32, 34 and 36 from the second side 20 of the arm board securement arrangement 10, as represented in FIG. 2. The longitudinal spacing "S" between the wrap members 24, 26, 28, 30 as well as between corresponding spacing between wrap members 32, 34 and 36 permits access to the exposed skin of the patient's arm PA secured therewithin, as is readily apparent from FIG. 2. Thus medicaments and surgical monitoring arrangements (built-in, or otherwise) may be utilized in conjunction with a comfortable securement arrangement for a patient's arm for a patient undergoing a surgical procedure.

Figure 3:
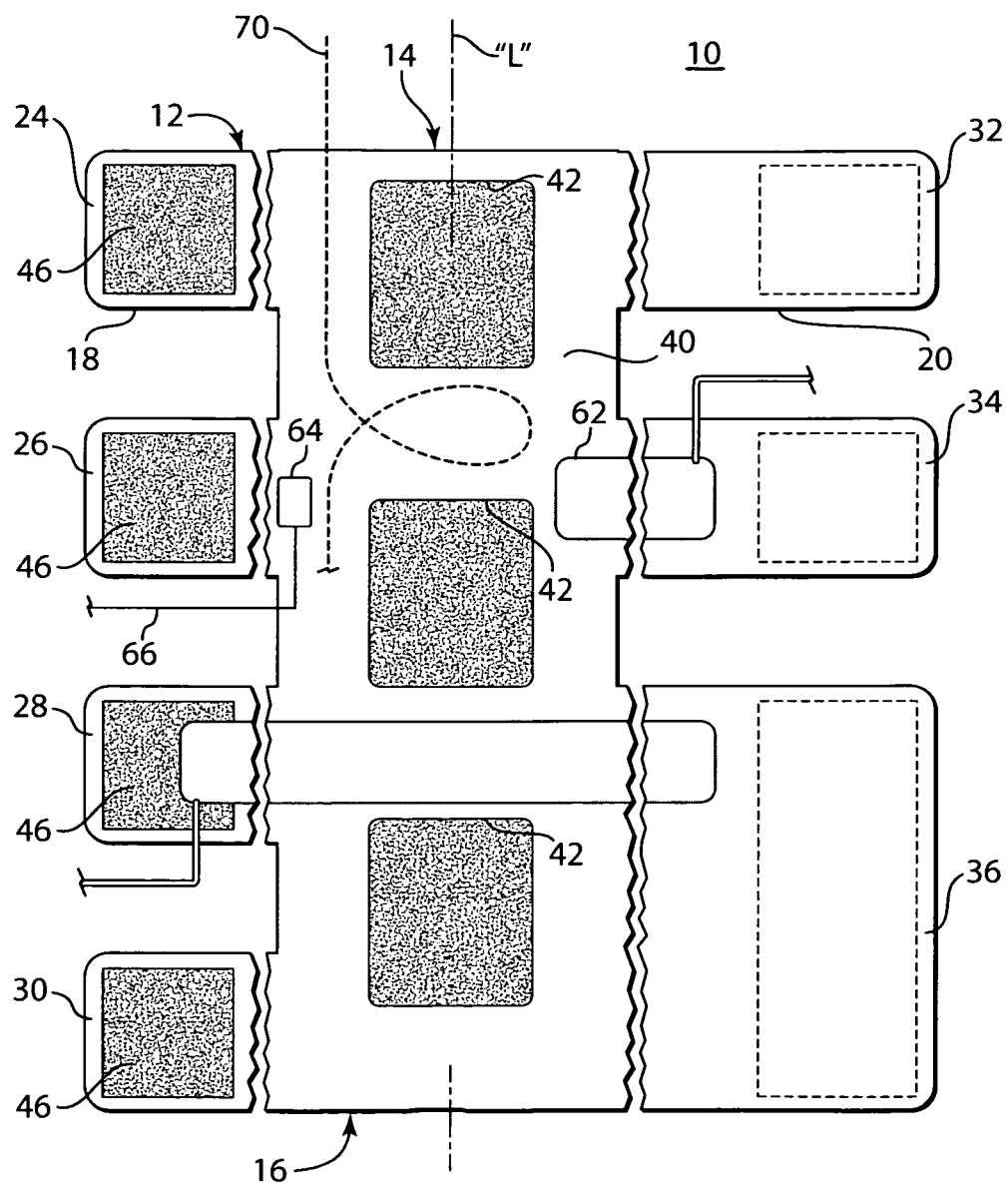
FIG. 3 is a plan view of the arm board securement arrangement similar to the view represented in FIG. 1, showing several further aspects of the present invention.

In a further embodiment of the present invention as represented in FIG. 3, the arm board securement arrangement 10 may include a built-in blood pressure monitor 60, a pulse oximeter 62, or a thermometer apparatus or medicament supply circuit 64 which may be connected to a proper control unit by a wireless controller or circuit 66 or the like, or may include or also comprise a properly supplied, securement arrangement built-in, controllable, limb temperature treating means 70 such as a patient cooling circuit or a patient heating circuit, represented in FIG. 3, to conveniently support, monitor and provide any needed treatment such as temperature control or medicament supply, to a patient undergoing a procedure on a surgical operating table utilizing the arm board securement arrangement of the present invention.

The invention claimed is:

1. An arm board securement arrangement for comfortably and safely securing a patient's arm to an arm board during an operative procedure, comprising:
   a flexible sheet of conformable material having a first end and a second end, and a first side and a second side with a central portion therebetween and a longitudinal axis extending therealong;
   a plurality of spaced apart wrap members extending on the first side from the central portion of the conformable material;
   a plurality of spaced apart wrap members extending on the second side from the central portion of the conformable material; and
   a gripping patch arranged on each of the wrap members to permit the wrap members to correspondingly engage one another upon the wrap members being wrapped about an arm of a patient; the central portion having a plurality of spaced apart openings therethrough; an elongated pillow for disposition upon an upper surface of the central portion for the resting of a patient's arm thereon, wherein the elongated pillow has a lower central portion engaging surface with gripping means thereon, to directly engage, through the plurality of spaced apart openings, a gripping means arranged upon an upper surface of an arm board on which the securement arrangement is placed.

2. The arm board securement arrangement as recited in claim 1, wherein the spaced apart wrap members on the first side are longer than the wrap members arranged on the second side of the central portion.

3. The arm board securement arrangement as recited in claim 1, wherein the central portion has the longitudinal axis extending therethrough, and which securement arrangement is about one and one-half feet long, about the length of an arm board.

4. The arm board securement arrangement as recited in claim 1, wherein a blood pressure sensor is arranged across the central portion to permit a patient's blood pressure to be monitored while the patient's arm is safely and comfortably secured to an arm board.

5. The arm board securement arrangement as recited in claim 1, wherein an oximeter is arranged across the central portion to permit a patient's blood to be monitored while the patient's arm is safely and comfortably secured to an arm board.

6. The arm board securement arrangement as recited in claim 1, wherein the wrap members are spaced apart about 2 inches to permit access to the patient's skin while the patient's arm is comfortably and safely secured to an arm board.

7. The arm board securement arrangement as recited in claim 1, wherein the wrap members of the first side of the central portion are about 3 inches wide to permit safe wrapping of a patient's arm and prevent digging in of a strap and hurt the patient's circulation.

8. A method of securing a patient's arm to an operating table's armboard extending therefrom, comprising:

placing a securement member of flexible sheet of conformable material having a first end and a second end, and a first side and a second side with a central portion therebetween and a longitudinal axis extending therealong onto an armboard of an operating table, the conformable material having a plurality of spaced apart wrap members extending on the first side from the central portion, with a plurality of spaced apart wrap members extending on the second side from the central portion, and a gripping patch arranged on each of the members to permit the members to correspondingly engage one another about an arm of a patient, the central portion having a plurality of spaced apart openings therethrough, and having an elongated pillow for disposition upon an upper surface of the central portion for the resting of a patient's arm thereon, wherein the elongated pillow has a lower central portion engaging surface with gripping means thereon, to directly engage, through the plurality of spaced apart openings, a gripping means to be arranged upon an upper surface of the arm board on which the securement member is placed;

wrapping the wrap members from the first side of the conformable material over on top of the patient's arm on the arm board;

wrapping the wrap members from the second side of the conformable material on top of the wrap members from the first side of the conformable material; and securing the wrap members from the first side onto the wrap members from the second side by interengagement with their respective gripping patches so as to hold the patient's arm to the arm board in a comfortable and secure manner.

9. The method as recited in claim 8, including:

installing a patient sensor onto the upper side of the conformable material to permit the patient's medical tests to be safely and easily run on the patient.

10. The method as recited in claim 9, including:

running a medical test on a patient secured to the armboard through the sensor incorporated onto the conformable material.

11. The method as recited in claim 8, including:

inserting the elongated pillow between the patient's arm and the conformable material.

12. The method as recited in claim 11, including:

attaching gripping securment means on the upper surface of the armboard.

13. The method as recited in claim 8, including:

changing the temperature of the patient by controlling an actuatable limb temperature treating circuit built into the securement arrangement.

* * * * *